(12) United States Patent
Iwase et al.

(10) Patent No.: US 10,552,672 B2
(45) Date of Patent: Feb. 4, 2020

(54) MEDICAL IMAGE PROCESSING APPARATUS, MEDICAL IMAGE PROCESSING METHOD, AND PROGRAM

(71) Applicant: CANON KABUSHIKI KAISHA, Tokyo (JP)

(72) Inventors: Yoshihiko Iwase, Yokohama (JP); Hiroshi Imamura, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 406 days.

(21) Appl. No.: 15/647,818

(22) Filed: Jul. 12, 2017

(65) Prior Publication Data
US 2017/0372132 A1 Dec. 28, 2017

Related U.S. Application Data

(60) Division of application No. 13/748,718, filed on Jan. 24, 2013, now abandoned, which is a continuation of
(Continued)

(30) Foreign Application Priority Data

Dec. 25, 2007 (JP) .................................. 2007-333193

(51) Int. Cl.
*G06K 9/00* (2006.01)
*G06F 19/00* (2018.01)
(Continued)

(52) U.S. Cl.
CPC ....... *G06K 9/00362* (2013.01); *G06F 19/321* (2013.01); *G06Q 10/10* (2013.01); *G06Q 50/22* (2013.01)

(58) Field of Classification Search
CPC ....... G06F 19/321; G06Q 10/10; G06Q 50/22
See application file for complete search history.

(56) References Cited

U.S. PATENT DOCUMENTS 8,560,341 B2   10/2013  Iwase et al.
2006/0277073 A1  12/2006  Heilbrunn et al.
(Continued)

FOREIGN PATENT DOCUMENTS

JP   05-205018 A   8/1993
JP   2001-187044 A   7/2001
(Continued)

OTHER PUBLICATIONS

Japanese Office Action dated Jan. 15, 2013 in corresponding Japanese Patent Application No. 2007-333193.

*Primary Examiner* — Neal Sereboff
(74) *Attorney, Agent, or Firm* — Carter, DeLuca & Farrell LLP

(57) ABSTRACT

A medical image processing apparatus includes a unit configured to analyze a target medical image, a unit configured to register information representing an aptitude of each doctor with respect to interpretation of a specific lesion and a modality used by each doctor, and a unit configured to, when the analysis result includes information associated with a lesion, decide an assigned doctor based on information representing the aptitude of each doctor with respect to interpretation of the specific lesion, and, when the analysis result includes no information associated with a lesion, decide an assigned doctor based on the modality.

16 Claims, 16 Drawing Sheets

Related U.S. Application Data application No. 12/810,141, filed as application No. PCT/JP2008/068475 on Oct. 10, 2008, now Pat. No. 8,560,341.

(51) Int. Cl.
*G06Q 10/10* (2012.01)
*G06Q 50/22* (2018.01)

(56) References Cited

U.S. PATENT DOCUMENTS

| | | |
|---|---|---|
| 2007/0053567 A1 | 3/2007 | Adachi et al. |
| 2008/0140454 A1 | 6/2008 | Hernandez et al. |
| 2008/0140723 A1 | 6/2008 | Hernandez et al. |
| 2013/0136326 A1 | 5/2013 | Iwase et al. |

FOREIGN PATENT DOCUMENTS

| | | |
|---|---|---|
| JP | 2002-109053 A | 4/2002 |
| JP | 2002-329190 A | 11/2002 |
| JP | 2004-105398 A | 4/2004 |
| JP | 2004-216008 A | 8/2004 |
| JP | 2005-065728 A | 3/2005 |
| JP | 2005-149108 A | 6/2005 |
| JP | 2006-130049 A | 5/2006 |
| JP | 2006-268075 A | 10/2006 |

F I G. 5

| INTERPRETING DOCTOR ID | MODALITY | | | REGION | | | EXPERIENCE | POST |
|---|---|---|---|---|---|---|---|---|
| 1 | CT | MRI | PET | CHEST REGION | ABDOMINAL REGION | HEAD REGION | 20 YEARS | ADVISING DOCTOR |
| 2 | CT | X-RAY | | CHEST REGION | ABDOMINAL REGION | | 2 YEARS | RESIDENT |
| 3 | X-RAY | MAMMO-GRAPHY | CT | CHEST REGION | ABDOMINAL REGION | | 12 YEARS | GENERAL |
| 4 | CT | X-RAY | MRI | CHEST REGION | ABDOMINAL REGION | | 10 YEARS | GENERAL |
| .... | | | | | | | | |

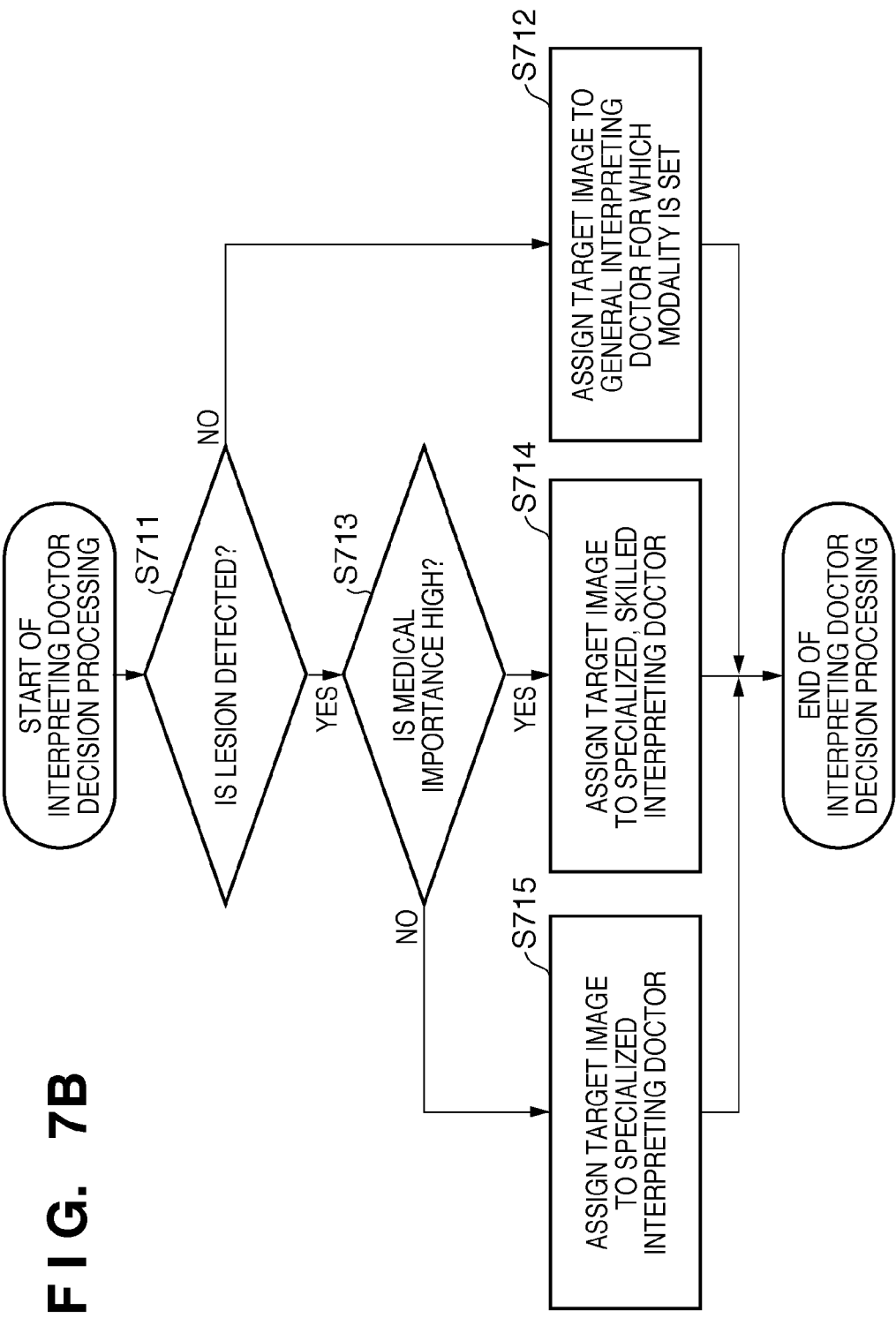

FIG. 10

| | |
|---|---|
| PATIENT A | INTERPRETING DOCTOR 1 |
| PATIENT B | INTERPRETING DOCTOR 1 |
| PATIENT C | INTERPRETING DOCTOR 1 |
| . . | . . |
| PATIENT K | INTERPRETING DOCTOR 3 |
| PATIENT L | INTERPRETING DOCTOR 3 |
| . . . . | . . . . |
| PATIENT X | INTERPRETING DOCTOR 2 |
| PATIENT Y | INTERPRETING DOCTOR 3 |

FIG. 12

| INTERPRET-ING DOCTOR ID | MODALITY | | | REGION | | | EXPERIENCE | POST | TIME SCHEDULE |
|---|---|---|---|---|---|---|---|---|---|
| 1 | CT | MRI | PET | CHEST REGION | ABDOMINAL REGION | HEAD REGION | 20 YEARS | ADVISING DOCTOR | 15:00~17:00 |
| 2 | CT | X-RAY | | CHEST REGION | ABDOMINAL REGION | | 2 YEARS | RESIDENT | 13:00~17:00 |
| 3 | X-RAY | MAMMO-GRAPHY | CT | CHEST REGION | ABDOMINAL REGION | | 12 YEARS | GENERAL | 13:00~15:00 |
| 4 | CT | X-RAY | MRI | CHEST REGION | ABDOMINAL REGION | | 10 YEARS | GENERAL | 13:00~17:00 |
| .... | | | | | | | | | |

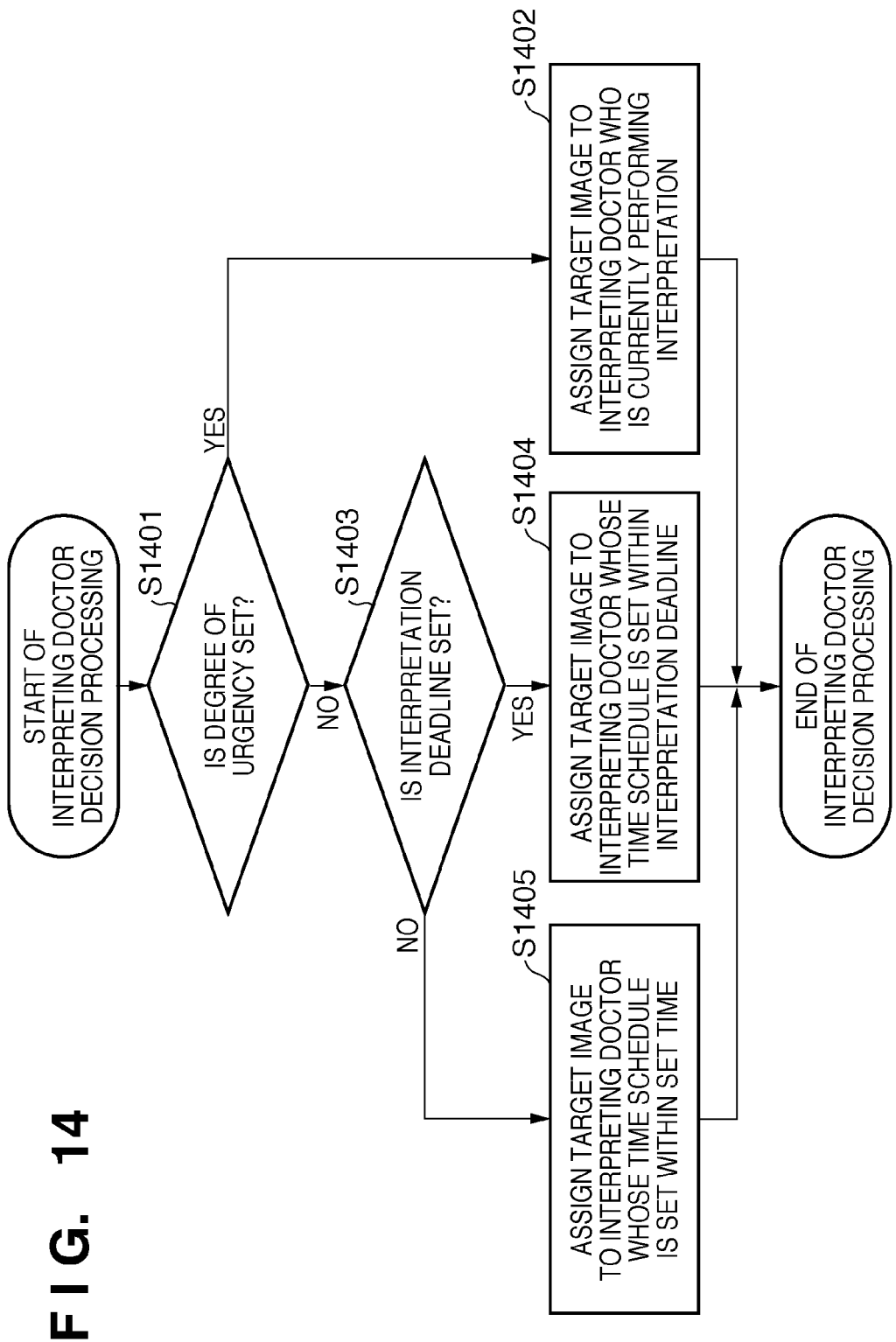

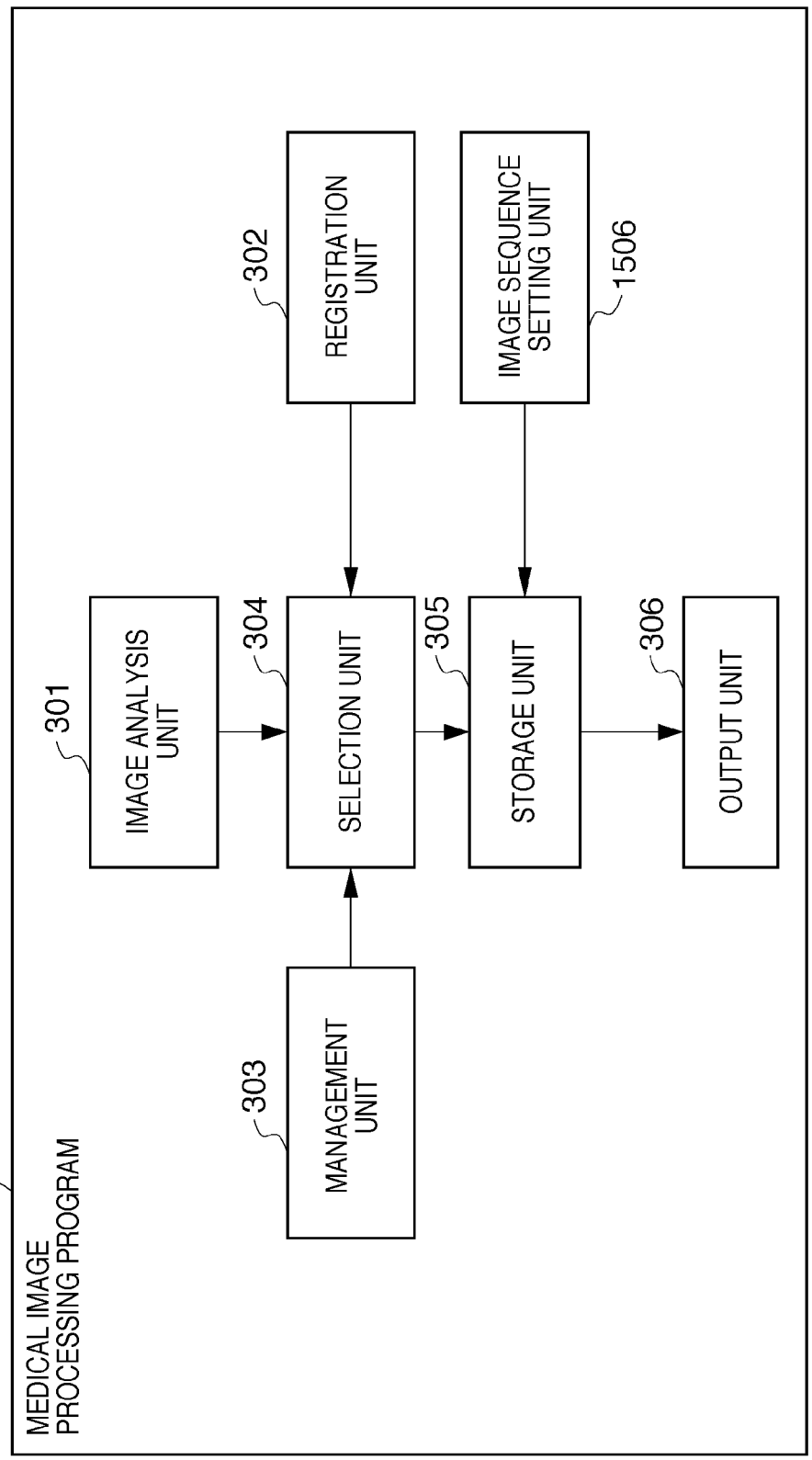

MEDICAL IMAGE PROCESSING APPARATUS, MEDICAL IMAGE PROCESSING METHOD, AND PROGRAM

CROSS REFERENCE TO RELATED APPLICATIONS

This application is a divisional of U.S. patent application Ser. No. 13/748,718, filed Jan. 24, 2013, which is a continuation of U.S. patent application Ser. No. 12/810,141, now U.S. Pat. No. 8,560,341, filed Jun. 22, 2010, which is a national stage application of PCT International Application No. PCT/JP2008/068475, filed Oct. 10, 2008, which claims the benefit of and priority to Japanese Patent Application No. 2007-333193, filed Dec. 25, 2007, the entire contents of each of which are hereby incorporated by reference herein in their entirety.

TECHNICAL FIELD

The present invention relates to a medical image processing technique for supporting the interpretation of medical images.

BACKGROUND ART

In the medical field, digitization of medical images obtained by imaging objects has been implemented. This makes it possible to display, on a monitor, the medical images obtained by using medical imaging apparatuses such as an X-ray apparatus, CR apparatus, CT apparatus, MRI apparatus, PET apparatus, ultrasonic apparatus, and OCT apparatus. A doctor then makes diagnosis of the state of a lesion and its change over time by interpreting the medical images displayed on the monitor. In this case, CR is an abbreviation for Computed Radiography, CT is an abbreviation for Computed Tomography, and MRI is an abbreviation for Magnetic Resonance Imaging. In addition, PET is an abbreviation for Positron Emission Tomography, and OCT is an abbreviation for Optical Coherence Tomography.

Conventionally, for the purpose of reducing the operation load on a doctor at the time of interpretation, a medical image processing apparatus has been developed, which is called a computer aided diagnosis apparatus (to be referred to as a CAD hereinafter) capable of automatically detecting lesions by analyzing medical images.

The CAD can detect, as a lesion, an abnormal tumor shadow representing a cancer or the like, a high-density minute calcified shadow, or the like based on an input medical image. Partly automating interpreting operation by a doctor in this manner can greatly reduce the operation load on the doctor at the time of interpretation.

In addition, with the aim of improving interpretation accuracy, for example, Japanese Patent Laid-Open No. 2006-130049 has proposed an arrangement configured to rearrange an interpretation sequence based on the detection result obtained by a CAD so as to sequentially interpret medical images, starting from a medical image including a lesion with a high malignancy grade. According to this arrangement, for example, it is possible to reduce the oversight of lesions by rearranging an interpretation sequence so as to allow a doctor to interpret medical images including lesions with high malignancy grades during a time of day in which the doctor feels less fatigue.

Furthermore, Japanese Patent Laid-Open No. 2004-216008 has proposed an arrangement configured to rearrange an interpretation sequence so as to allow a doctor to continuously interpret the same region, as well as rearranging an interpretation sequence in accordance with malignancy grades as described above. According to this arrangement, it is possible to further reduce the oversight of lesions.

All the inventions disclosed in the respective patent references described above are based on the premise that one doctor interprets all medical images. In general, however, a plurality of doctors serve in a hospital, center, or the like. In this case, these doctors often share in interpreting a plurality of medical images.

When a plurality of doctors serve as in this case, the respective doctors often specialize in different fields. Even if the doctors specialize in the same field, they often vary in years of experience. For this reason, how to assign a plurality of medical images to the respective doctors will greatly influence the overall operating efficiency and interpretation accuracy in the hospital or center.

The present invention has been made in consideration of the above problem, and has as its object to improve interpretation accuracy, as well as overall operating efficiency, when a plurality of doctors share in interpreting a plurality of medical images.

SUMMARY OF THE INVENTION

In order to achieve the above object, a medical image processing apparatus according to the present invention has the following arrangement. That is, the apparatus is a medical image processing apparatus which decides assigned doctors so as to allow a plurality of doctors to share in interpreting a plurality of medical images obtained by imaging an object using a medical imaging apparatus, the apparatus comprising an analysis unit configured to analyze a medical image, of the plurality of medical images, which serves as an assignment target, and outputting an analysis result, an acquisition unit configured to acquire information associated with a medical imaging apparatus used to obtain the medical image as the assignment target, a registration unit configured to register information representing an aptitude of each doctor with respect to interpretation of a specific lesion and information representing an aptitude of each doctor with respect to interpretation of a medical image obtained by imaging by a specific medical imaging apparatus, and a decision unit configured to, when the analysis result obtained by the analysis unit includes information associated with a lesion, decide an assigned doctor for the medical image as the assignment target based on information which is registered by the registration unit and represents an aptitude of each doctor with respect to interpretation of a specific lesion, and, when the analysis result obtained by the analysis unit includes no information associated with a lesion, decide an assigned doctor for the medical image as the assignment target based on information which is registered by the registration unit and represents an aptitude of each doctor with respect to interpretation of a medical image obtained by imaging by a specific medical imaging apparatus.

According to the present invention, it is possible to improve interpretation accuracy, as well as overall operating efficiency, when a plurality of doctors share in interpreting a plurality of medical images.

Other features and advantages of the present invention will be apparent from the following description taken in conjunction with the accompanying drawings, in which like reference numerals designate the same or similar parts throughout the figures thereof.

BRIEF DESCRIPTION OF DRAWINGS

The accompanying drawings, which are incorporated in and constitute a part of the specification, illustrate embodiments of the invention and, together with the description, serve to explain the principles of the invention.

FIG. 5 is a view showing an example of the interpreting doctor information managed by a management unit 303;

FIG. 7B is a flowchart showing the detailed processing sequence of interpreting doctor decision processing;

FIG. 10 is a view showing an example of patient lists;

FIG. 12 is a view showing an example of the interpreting doctor information managed by the management unit 303;

FIG. 14 is a flowchart showing the detailed processing sequence of interpreting doctor decision processing;

FIG. 15 is a functional block diagram showing the functions implemented by a medical image processing program according to the fourth embodiment of the present invention;

DETAILED DESCRIPTION OF THE EMBODIMENTS

The best mode for carrying out the present invention will be described in detail below with reference to the accompanying drawings.

First Embodiment

1. Arrangement of Medical Image Processing System

Figure 1:
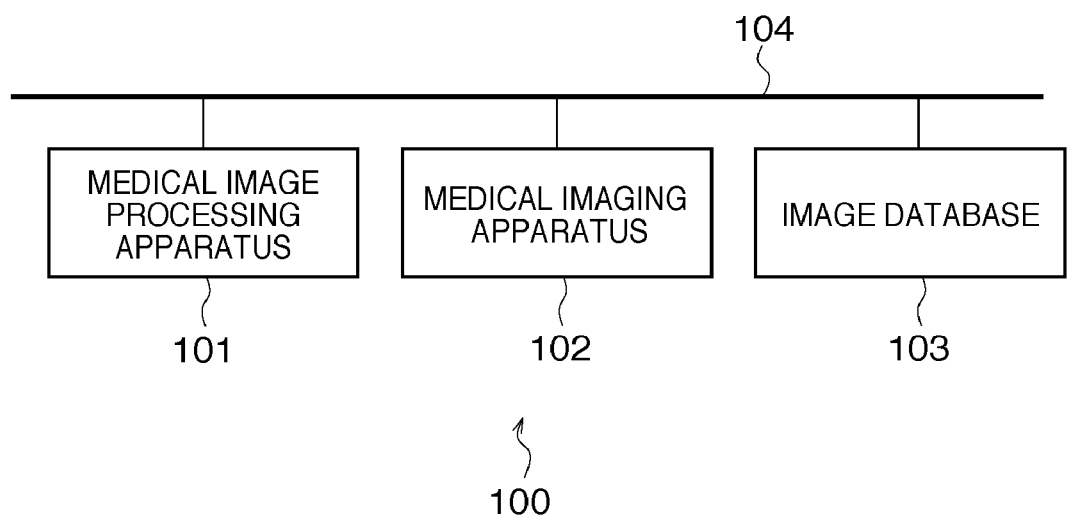
FIG. 1 is a block diagram showing the arrangement of a medical image processing system 100 including a medical image processing apparatus according to the first embodiment of the present invention.

FIG. 1 is a block diagram showing the arrangement of a medical image processing system 100 including a medical image processing apparatus according to the first embodiment of the present invention.

As shown in FIG. 1, the medical image processing system includes a medical image processing apparatus 101, a medical imaging apparatus 102, and an image database 103, which are communicably connected to each other via a network 104.

The medical imaging apparatus 102 is an apparatus to generate medical images by imaging an object (patient), and includes an X-ray apparatus, CR apparatus, CT apparatus, MRI apparatus, PET apparatus, ultrasonic diagnosis apparatus, and OCT apparatus.

The image database 103 stores the medical image obtained by the medical imaging apparatus 102 upon adding additional information. Additional information includes an imaging modality, imaging date and time, degree of urgency, interpretation deadline, examination purpose, imaging region, anamnesis, age, sex, smoking history, finding, chief complaint, examination result, hospital name, and patient name and birth date.

The medical image processing apparatus 101 is an apparatus for displaying a medical image obtained by the medical imaging apparatus 102 or a medical image stored in the image database 103 and also inputting the result of interpretation by a doctor based on the displayed medical image as character information to create a report.

2. Hardware Arrangement of Medical Image Processing Apparatus 101

Figure 2:
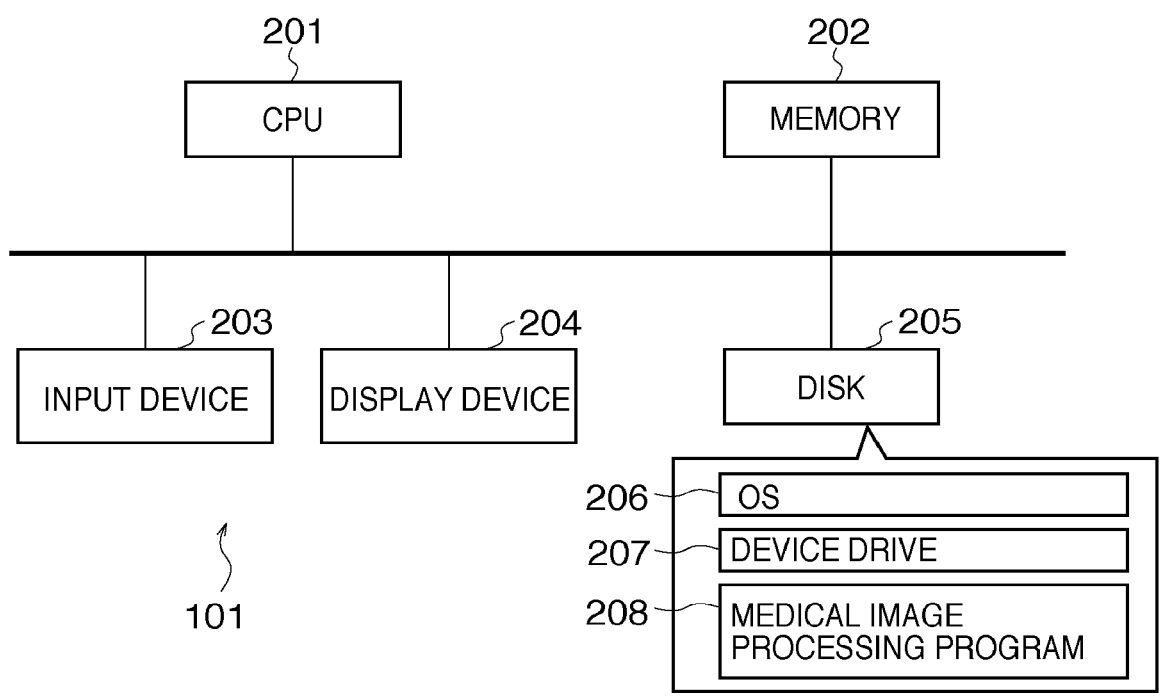
FIG. 2 is a block diagram showing the hardware arrangement of a medical image processing apparatus 101.

FIG. 2 is a block diagram showing the hardware arrangement of the medical image processing apparatus 101. As shown in FIG. 2, the medical image processing apparatus 101 includes, as constituent elements, a CPU (Central Processing Unit) 201, an input device 203, a display device 204, a memory 202, and a disk 205.

The CPU 201 executes various control programs and controls the operation of each constituent element of the medical image processing apparatus 101. The input device 203 accepts the pointing input by a doctor and the input of characters and the like. The display device 204 displays the results obtained when the CPU 201 executes various control programs. The display device 204 includes, for example, a CRT monitor or a liquid crystal monitor.

The memory 202 stores a predetermined control program and provides a work area at the time of execution of the control program. The disk 205 stores an operating system (OS) 206, device drives 207 for peripheral devices, and various control programs such as a control program (to be referred to as a "medical image processing program" 208) for implementing a medical image processing method according to the present invention.

3. Overall Functional Block of Medical Image Processing Program 208

Figure 3:
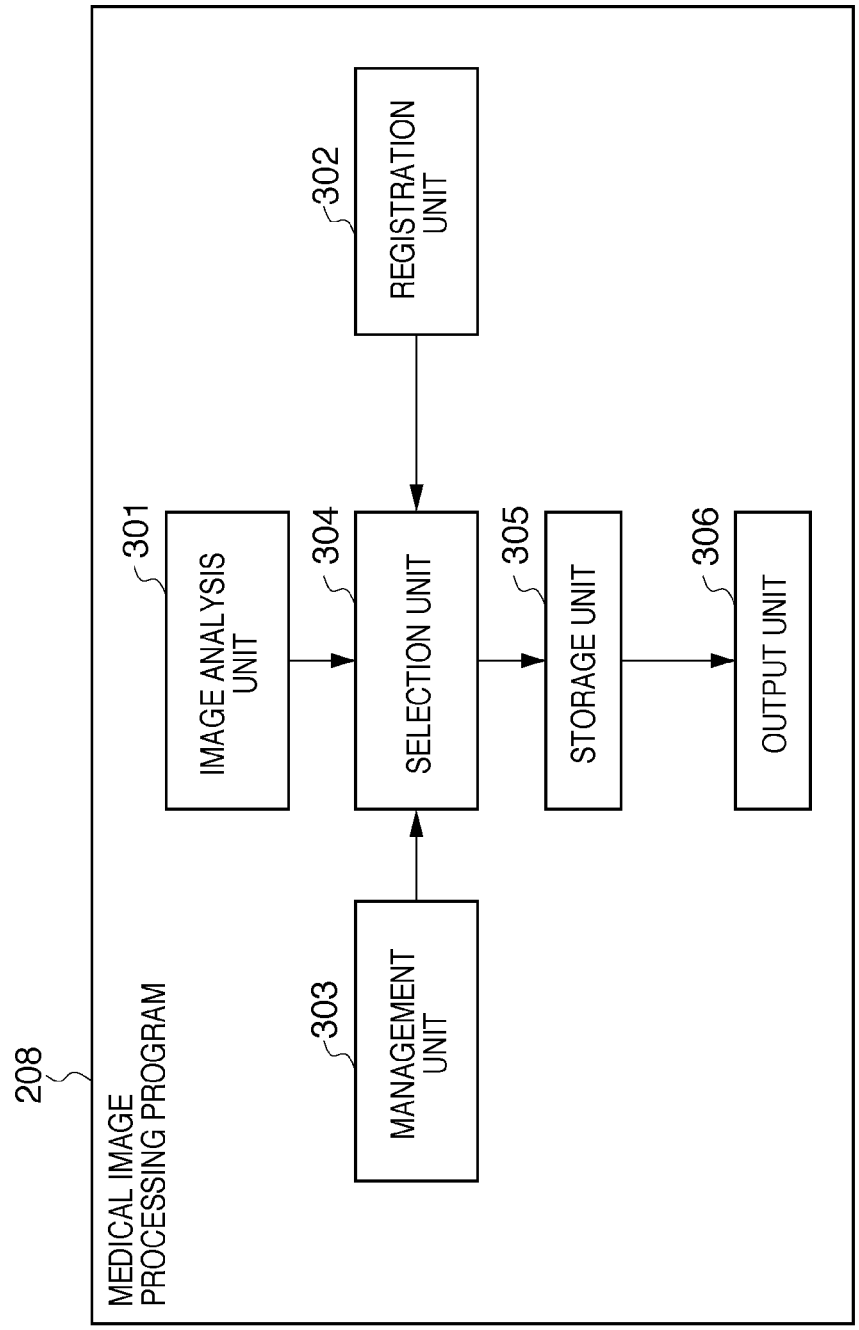
FIG. 3 is a functional block diagram showing the functions implemented by a medical image processing program 208.

FIG. 3 is a functional block diagram showing the functions implemented by the medical image processing program 208. As shown in FIG. 3, the medical image processing program 208 includes an image analysis unit 301 to analyze the medical images stored in the image database 103, a registration unit 302 to register a doctor who performs interpretation (interpreting doctor), and a management unit 303 to manage interpreting doctor information.

The medical image processing program 208 also includes a selection unit 304 to decide assigned doctors to be respectively assigned with a plurality of medical images to be interpreted, based on the analysis result obtained by the image analysis unit 301 and the interpreting doctor information managed by the management unit 303. The selection unit 304 further generates a patient list containing an array of patient IDs corresponding to the medical images assigned to each interpreting doctor.

The medical image processing program 208 further includes a storage unit 305 to store, in the disk 205, the patient list generated by the selection unit 304 for each interpreting doctor, and an output unit 306 to display the patient lists on the display device 204. Each unit will be described in detail below.

4. Image Analysis Unit

The image analysis unit 301 analyzes a medical image and detects an organ region and/or a lesion (outputs, as an analysis result, information associated with a lesion, for example, a lesion probability, malignancy grade, identification difficulty, and medical importance).

4.1 Detection of Organ Region

In the case of a chest CT image, for example, the detection of an organ region is the detection of a region including a lung field, diaphragm, bronchus, pulmonary artery, and pulmonary vein. This also includes the classification of a detected lung field into segments including a superior lobe, median lobe, and inferior lobe. Note, however, that the types of organ regions to be detected are not limited to them.

Note that as methods for detecting organ regions from medical images, various methods are available. Assume that this embodiment uses the level set method, which is one of the dynamic contour methods. In the case of the level set method, a level set function which is one dimension higher than that of an organ region as a detection target is defined, and the organ region as the detection target is regarded as the zero contour line of the function. The contour is then controlled to detect an organ region by updating this function based on the following evolution equation called the level set equation.

$$\varphi_t + F|V_\varphi| = 0$$

where $\varphi_t$ represents the value obtained by primary differentiation of the level set function in the time axis direction, F represents the growth rate of the contour, and $|V_\varphi|$ represents the absolute value of the gradient of the level set function. In this manner, an organ region is detected from the medical image.

Note that the method to be used to detect an organ region is not limited to the level set method. For example, it is possible to use a method based on threshold processing, region growing method, dynamic contour method, method based on clustering, minimum graph cut method, or the like. It is also possible to use other methods.

It is also possible to selectively use these methods in accordance with the organ region to be detected.

In addition, it is possible to use a probability atlas, human figure model, or the like instead of using only an image feature amount, when detecting an organ region.

4.2 Lesion Detection

When detecting a lesion from an organ region, first of all, the image analysis unit 301 detects an abnormal portion by detecting a difference by, for example, filter processing, pattern matching processing, or registration processing for a past image, average shape image, or the like and a medical image.

More specifically, filter processing uses, for example, a filter in consideration of a shape or the direction of a gradient vector.

A feature amount is then extracted by detecting an abnormal portion using one of these processes or other processes. Note that the feature amount extracted at this time includes the feature amount based on a pixel value, for example, a CT value average, CT value variance/standard deviation, maximum/minimum CT value, contrast, energy, or entropy. This feature amount also includes the feature amount based on a shape, for example, a peround, surface area, volume, sphericity, irregularity, average curvature, principal curvature, Gaussian curvature, or maximum diameter. Assume that this embodiment extracts at least one or a combination of the above feature amounts.

The image analysis unit 301 performs processing for determining whether a detected abnormal portion is a lesion (lesion probability), identifying, if it is a lesion, the type of lesion, and also identifying a malignancy grade for categorizing the lesion as a malignant or benign lesion and medical importance.

Figure 4A:
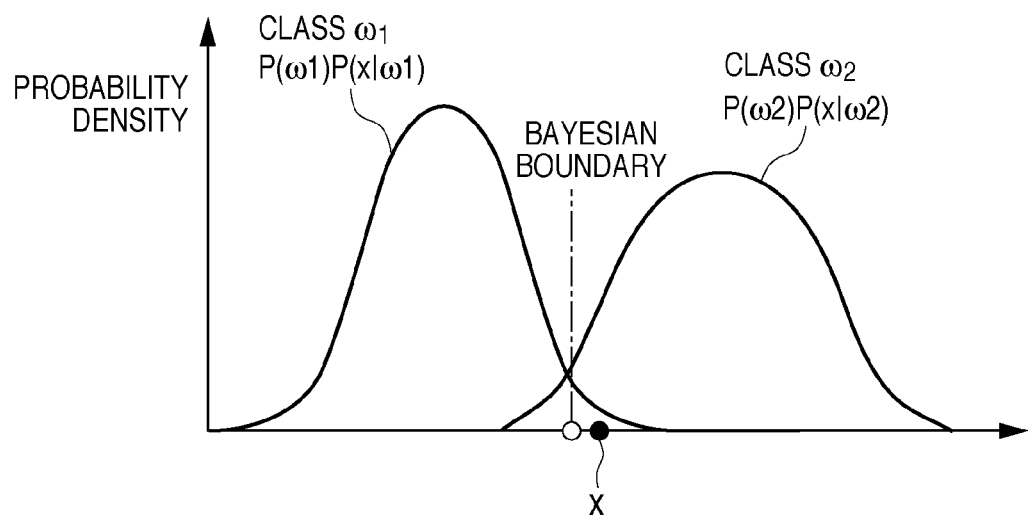
FIG. 4A is a graph for explaining identification processing based on the least squares method and the Bayes decision rule.
Figure 4B:
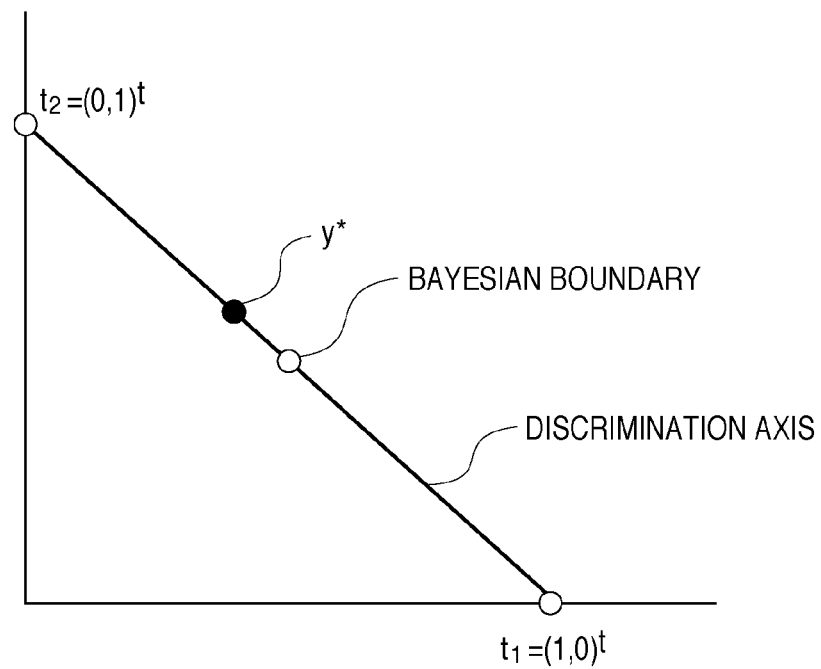
FIG. 4B is a graph for explaining identification processing based on the least squares method and the Bayes decision rule.

A case in which the processing for determining whether a detected abnormal portion is a lesion or identifying the malignancy grade of a lesion (whether it is malignant or benign) and the identification difficulty of the lesion is performed by using the least squares method and the Bayes decision rule will be described with reference to FIGS. 4A and 4B. The malignancy grades to be identified are classified into classes $\omega_1$ and $\omega_2$, and will be described by using the feature space in FIG. 4A and the discrimination space in FIG. 4B.

An input given pattern x (the feature amount of a target medical image) is transferred to a Bayesian probability vector whose ith component is the Bayesian posterior probability of a class $\omega_i$ according to optimal mapping $y_i^+ = \phi^*(x_i)$.

A Bayesian boundary in the feature space corresponds to a simple barycentric subdivision boundary in the (c−1)th dimension, and corresponds to a simple linear identification boundary in the discrimination space. Reference symbol $t_i$ denotes a representative point in each class in the discrimination space. The square distance between $y^+$ and $t_i$ on a discrimination plane is given by the following equation.

$$D_i = \|y^* - t_i\|^2 = \|y^*\| - 2P(\omega_i|x) + 1$$

Selecting a class so as to minimize the square distance between $y^*$ and $t_i$, therefore, can identify a specific class to which the input pattern x belongs.

Letting $D_1$ be the distance between the input pattern x and the class $\omega_1$ and $D_2$ be the distance between the input pattern x and the class $\omega_2$, it is possible to obtain the distance from the Bayesian boundary by using the likelihood ratio. In this case, the likelihood ratio is expressed by $D_1/D_2$. That is, as the likelihood ratio increases, the probability that the input pattern belongs to the class $\omega_2$ increases. As the likelihood ratio decreases, the probability that the input pattern belongs to the class $\omega_1$ increases. As this radio approaches 1, the pattern approaches the Bayesian boundary. There is a possibility that the image analysis unit 301 will erroneously identify the pattern x near the Bayesian boundary. In addition, it may be difficult for an interpreting doctor to perform determination when performing interpretation. For this reason, a flag is set for a medical image including a lesion within a predetermined distance from the Bayesian boundary to indicate that identification is difficult. In this case, for example, a threshold Th of likelihood ratio by which difficulty of identification is determined is set to 0.9<Th<1.1.

In this manner, identification processing can be performed by using the feature amount extracted from a medical image. Although the identification processing described above uses the least squares method and Bayes decision rule, the present invention is not limited to this. For example, this processing can use a linear discrimination method, support vector machine, AdaBoost, neural network, or the like.

5. Registration Unit

The registration unit 302 will be described next. The registration unit 302 registers interpreting doctors who share in interpreting medical images and interpreting doctor information based on the analysis result obtained by the image analysis unit 301. An interpreting doctor is registered when the doctor logs in to the medical image processing apparatus 101 to interpret a medical image. A registered interpreting doctor is deregistered when the doctor logs out the medical image processing apparatus 101.

Assume that interpreting doctor information can be registered in advance, during interpretation, or by learning. Assume also that an authenticated person or a third person authorized to register can perform registration. Note that it is also possible to register interpreting doctor information by, for example, accessing an external storage terminal and acquiring interpreting doctor information.

6. Management Unit

The management unit 303 will be described next. The management unit 303 manages the interpreting doctor information registered by the registration unit 302. Even after an interpreting doctor logs out the medical image processing apparatus 101, the management unit 303 keeps recording interpreting doctor information on a disk, together with the ID information of the interpreting doctor.

The selection unit 304 uses the interpreting doctor information managed by the management unit 303 to decide assigned doctors when assigning medical images to the respective interpreting doctors.

FIG. 5 is a view showing an example of the interpreting doctor information managed by the management unit 303. As shown in FIG. 5, interpreting doctor information includes a modality in which each interpreting doctor excels (information indicating the aptitude of each interpreting doctor with respect to the interpretation of medical images obtained by a specific medical imaging apparatus). The interpreting doctor information also includes information indicating the aptitude of each interpreting doctor with respect to the interpretation of a specific lesion, for example, the specialized field of each interpreting doctor, the doctor's speciality in region/disease, years of experience, and post.

7. Selection Unit

Figure 6:
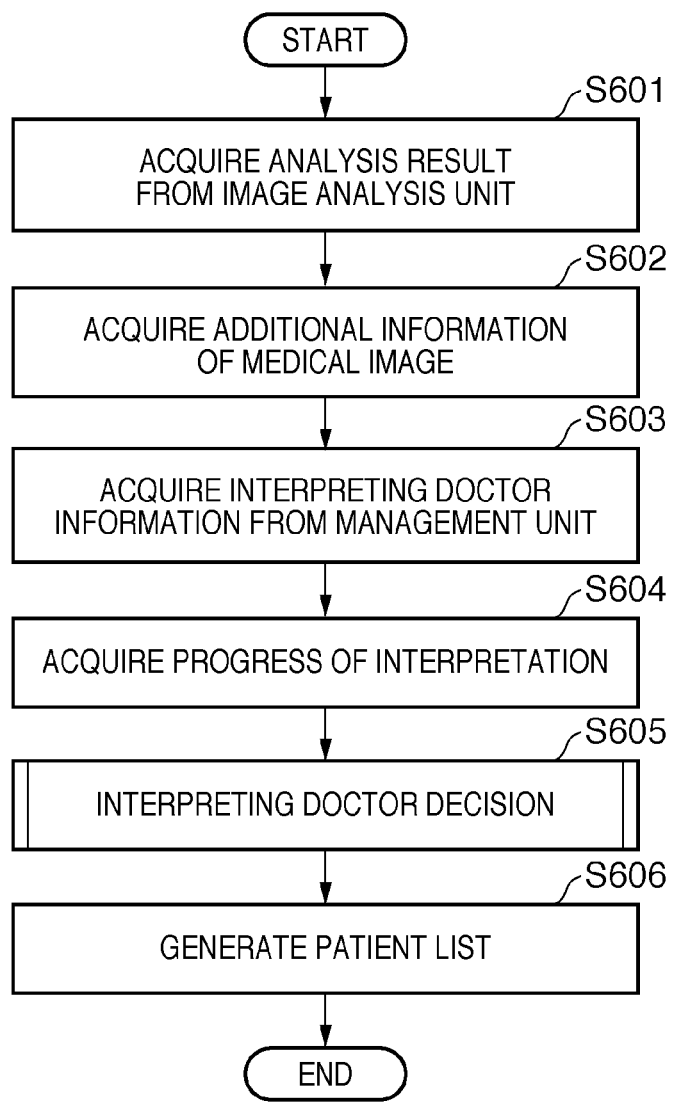
FIG. 6 is a flowchart showing a processing sequence in a selection unit 304.

A processing sequence in the selection unit 304 will be described next with reference to the flowchart of FIG. 6. In step S601, the selection unit 304 acquires, as an analysis result, at least one or a combination of the organ region, lesion probability, type of lesion, identification difficulty, malignancy grade, and medical importance detected by the image analysis unit 301.

In step S602, the selection unit 304 acquires, as additional information of a medical image, an imaging modality (information associated with a medical image apparatus), imaging date and time, degree of urgency, interpretation deadline (information associated with a temporal limitation), examination purpose, imaging region, anamnesis, age, sex, smoking history, finding, chief complaint, and examination result. Assume that additional information to be acquired is at least one or a combination of these pieces of information.

In step S603, the selection unit 304 acquires interpreting doctor information of the interpreting doctor who is currently performing interpretation from the management unit 303. The interpreting doctor information includes at least one or a combination of the specialized field of the interpreting doctor or the modality in which the doctor excels, doctor's speciality in the region/disease, the years of experience, and the post.

In step S604, the storage unit 305 acquires information associated with the progress of interpretation by an interpreting doctor who is currently performing interpretation from the storage unit 305. The information associated with the progress of interpretation includes the number of patients pooled in a patient list and at least one or a combination of the average value, maximum value, and minimum value of interpretation times required to interpret medical images of one patient.

In step S605, the selection unit 304 decides interpreting doctors for medical images as assignment targets, based on the information acquired in steps S601 to S604. Note that the details of the processing for deciding interpreting doctors for medical images as assignment targets (interpreting doctor decision processing) will be described later.

In step S606, the selection unit 304 generates a patient list for displaying a list of patients corresponding to medical images assigned to the respective interpreting doctors based on the interpreting doctor decision processing result in step S605 (patient list generation processing). Note that the details of the patient list generation processing will be described later.

7.1 Details (1) of Interpreting Doctor Decision Processing (Step S605)

Figure 7A:
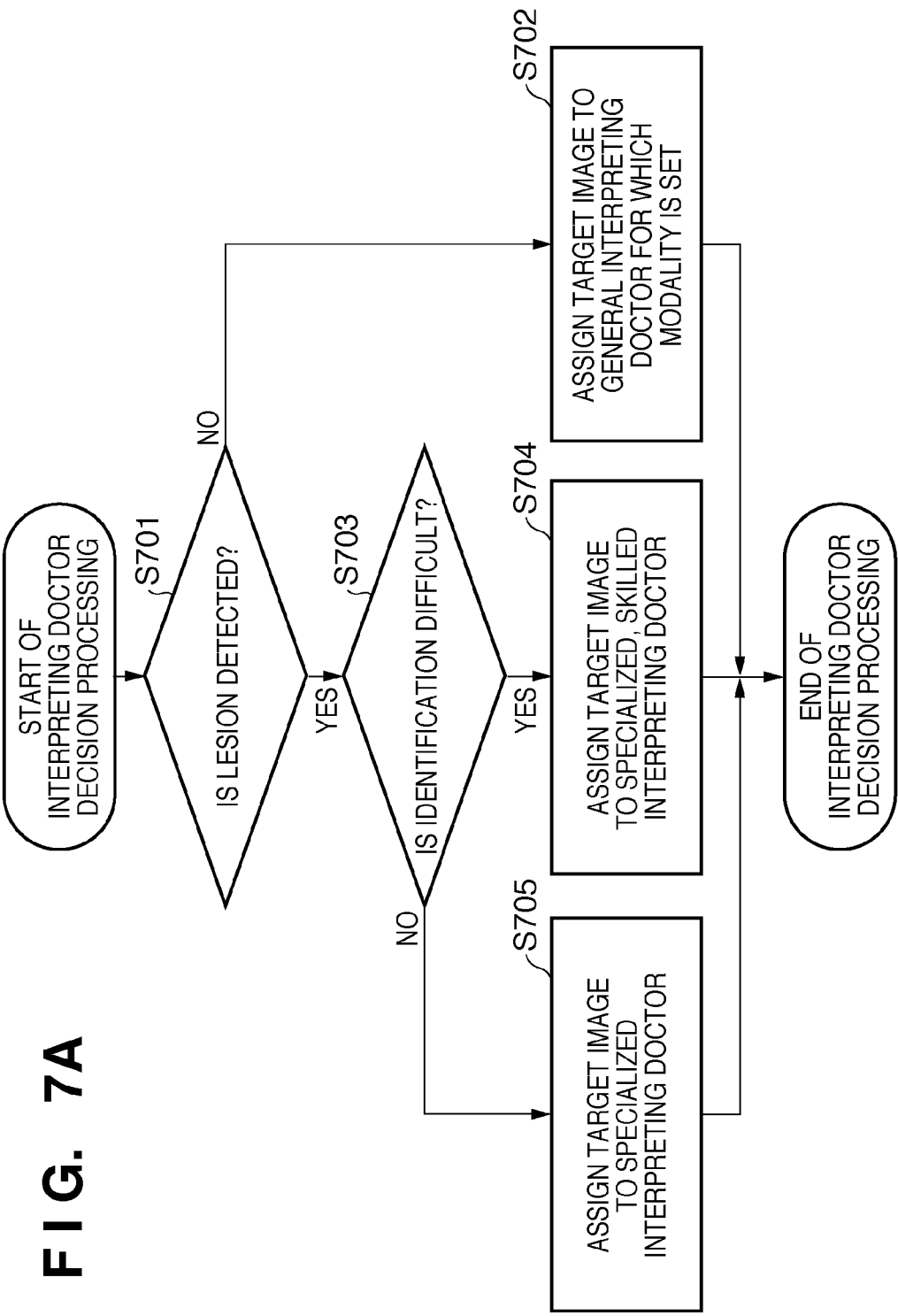
FIG. 7A is a flowchart showing the detailed processing sequence of interpreting doctor decision processing.

FIG. 7A is a flowchart showing the detailed processing sequence of interpreting doctor decision processing (step S605). In step S701, it is determined whether the image analysis unit 301 has detected a lesion on a medical image as an assignment target.

If it is determined in step S701 that no lesion has been detected, the process advances to step S702 to assign the medical image as the assignment target to a general interpreting doctor for which a corresponding modality is set.

If it is determined in step S701 that a lesion has been detected, the process advances to step S703 to determine whether the image analysis unit 301 has determined that the lesion is difficult to identify.

If it is determined in step S703 that the lesion is difficult to identify, the process advances to step S704 to assign the medical image as the assignment target to a skilled interpreting doctor specializing in the corresponding field.

If it is determined in step S703 that the lesion is not difficult to identify, the process advances to step S705 to assign the medical image as the assignment target to an interpreting doctor specializing in the corresponding field.

Performing interpreting doctor decision processing in this manner will assign medical images as assignment targets to suitable interpreting doctors.

A specific example of the above interpreting doctor decision processing will be described below in correspondence with an example of the interpreting doctor information in FIG. 5.

If, for example, a lung cancer has been detected on a chest CT image, and the image analysis unit 301 has determined that the lesion is not difficult to identify (no flag is set), interpreting doctors 1 to 3 are selected as interpreting doctors specializing in the region in which the lesion has been detected.

In contrast, if a lung cancer has been detected on a chest CT image, and the image analysis unit 301 has determined that the lesion is difficult to identify (a flag is set), interpreting doctor 1 is selected as a skilled interpreting doctor specializing in the region in which the lesion has been detected.

If no lesion has been detected on the chest CT image, interpreting doctors 1 to 4 are selected as interpreting doctors corresponding to interpreting doctor information in which the modality which has obtained the medical image is set.

7.2 Details (2) of Interpreting Doctor Decision Processing (Step S605)

FIG. 7B is a flowchart showing another detailed processing sequence of interpreting doctor decision processing. In step S711, it is determined whether the image analysis unit 301 has detected a lesion on a medical image as an assignment target.

If it is determined in step S711 that no lesion has been detected, the process advances to step S712 to assign a medical image as an assignment target to a general interpreting doctor for which a corresponding modality is set.

If it is determined in step S711 that a lesion has been detected, the process advances to step S713 to determine whether the lesion is a lesion with a high medical importance. A medical importance is a degree indicating the possibility that the lesion may endanger the life of the patient. A lesion which is likely to endanger the life is determined as a lesion with a high medical importance.

If it is determined in step S713 that the lesion is a lesion with a high medical importance, the process advances step S714 to assign the medical image as the assignment target to a specialized, skilled interpreting doctor.

If it is determined in step S713 that the lesion is a lesion with a low medical importance, the process advances to step S715 to assign the medical image as the assignment target to a specialized interpreting doctor.

Performing interpreting doctor decision processing in this manner will assign medical images as assignment targets to suitable interpreting doctors.

A specific example of the above interpreting doctor decision processing will be described below in correspondence with an example of the interpreting doctor information in FIG. 5.

If, for example, a lung cancer is detected on a chest CT image, interpreting doctor 1 or interpreting doctor 3 is selected.

In contrast, if pneumonia is detected on a chest CT image, interpreting doctor 2 is selected for the following reason. In general, a lung cancer is higher in medical importance than pneumonia. In addition, a malignant disease is higher in medical importance than a benign disease.

7.3 Details of Patient List Generation Processing (Step S606)

Figure 8:
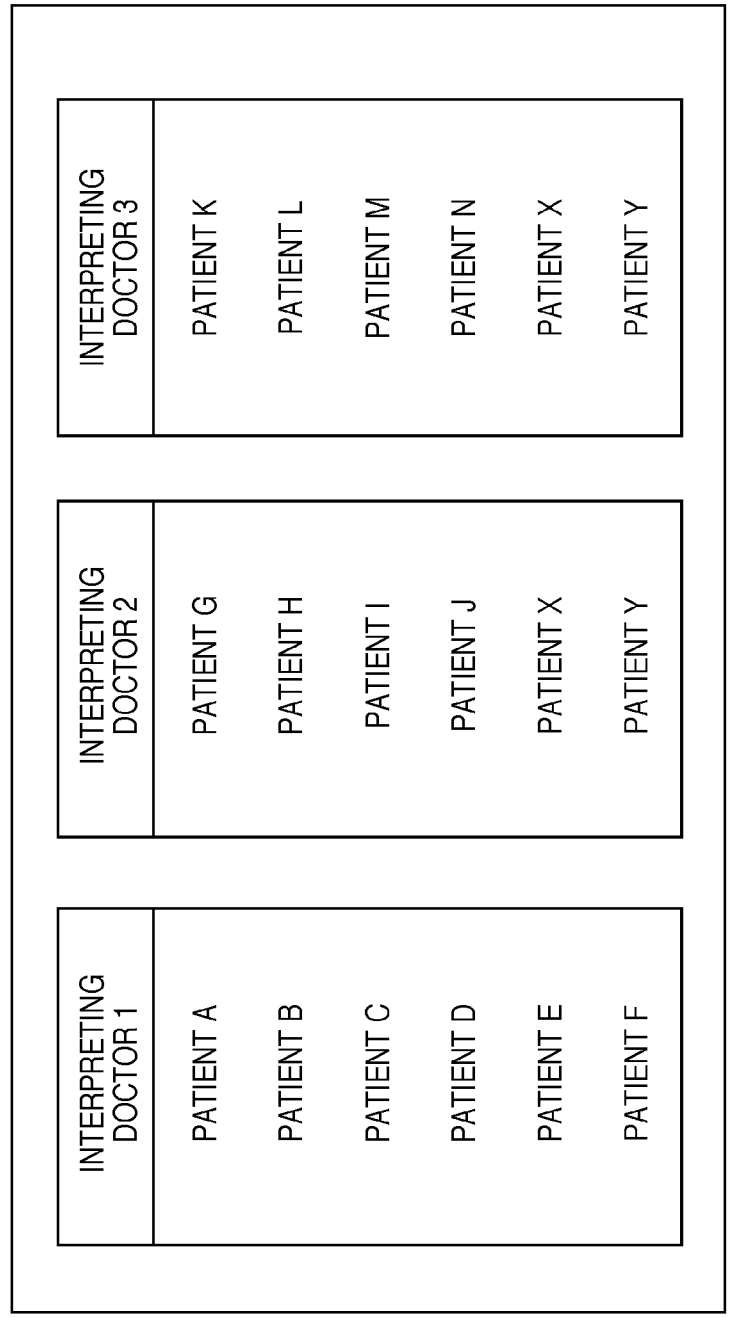
FIG. 8 is a view showing an example of patient lists.

FIG. 8 is a view showing an example of a patient list set for each interpreting doctor. A patient list is a list indicating the correspondence relationship between each interpreting doctor and medical image IDs, with the IDs being ordered in the interpretation sequence. Patient lists are generated based on interpreting doctor information, and hence differ for the respective interpreting doctors.

The order of patient IDs corresponding to medical images which are arrayed in a patient list is decided based on the scores calculated by comparing the additional information of each medical image and the analysis result obtained by the image analysis unit 301 with the interpreting doctor information.

More specifically, positive points are added to scores in accordance with the degrees of urgency, identification difficulties, the medical importances of lesions, and the like.

Patient IDs corresponding to medical images with higher calculated scores are arrayed at higher positions in the patient list. Consider, for example, a chest CT image on which a lung cancer is detected, and a chest CT image on which pneumonia is detected. In this case, a patient ID corresponding to the medical image on which the lung cancer has been detected is placed at a higher position in the patient list.

Note that it is possible to assign a weight to a point to be added in accordance with the experience or post of each interpreting doctor when calculating a score so as to set higher points for interpreting doctors with higher skills.

With this arrangement, when the same medical image is assigned to a plurality of interpreting doctors, since the medical image is set in the patient list for a skilled interpreting doctor is higher in position than in the patient list for a general interpreting doctor, it is possible to make a more specialized interpreting doctor interpret a medical image including a lesion which is difficult to identify.

Note that in the case shown in FIG. 8, patients X and Y are arrayed at lower positions in both the patient lists for interpreting doctors 2 and 3. This is a case in which the same medical images are arrayed in the list for an interpreting doctor other than skilled interpreting doctors. Assume that in this case, when one of the interpreting doctors performs interpretation first, patients X and Y are deleted from the patient list for the other interpreting doctor.

As described above, even if the order of patients in a patient list is decided once, the order is not fixed but is changed in accordance with the progress of interpretation by the interpreting doctor. According to this arrangement, if, for example, an interpreting doctor has not started interpreting a medical image with a high degree of urgency a predetermined period of time before the deadline, it is possible to perform control to interchange the position of the patient ID corresponding to the medical image with a higher position in the patient list.

8. Storage Unit

The storage unit 305 will be described next. The storage unit 305 stores the patient list generated by the selection unit 304 for each interpreting doctor. The storage unit 305 stores in advance, in the disk 205, the medical images assigned to only a specific interpreting doctor and the medical images assigned to many interpreting doctors. With regard to a medical image assigned to many interpreting doctors, when a given interpreting doctor interprets the image first, the image is deleted from the patient lists for the remaining interpreting doctors.

9. Output Unit

The output unit 306 will be described next. The output unit 306 displays medical images on the display device 204 in the order of the patient list generated by the selection unit 304. Note that patient lists can be displayed to allow interpreting doctors and third persons to check the interpretation sequence, or can be internally stored without being displayed.

On displayed patient lists or medical images, marks are displayed to differentiate medical images assigned to only specific interpreting doctors from medical images assigned to many interpreting doctors.

Assume also that a mark is displayed on a medical image for which a degree of urgency or an interpretation deadline is set, in order to differentiate it from other medical images.

Figure 9:
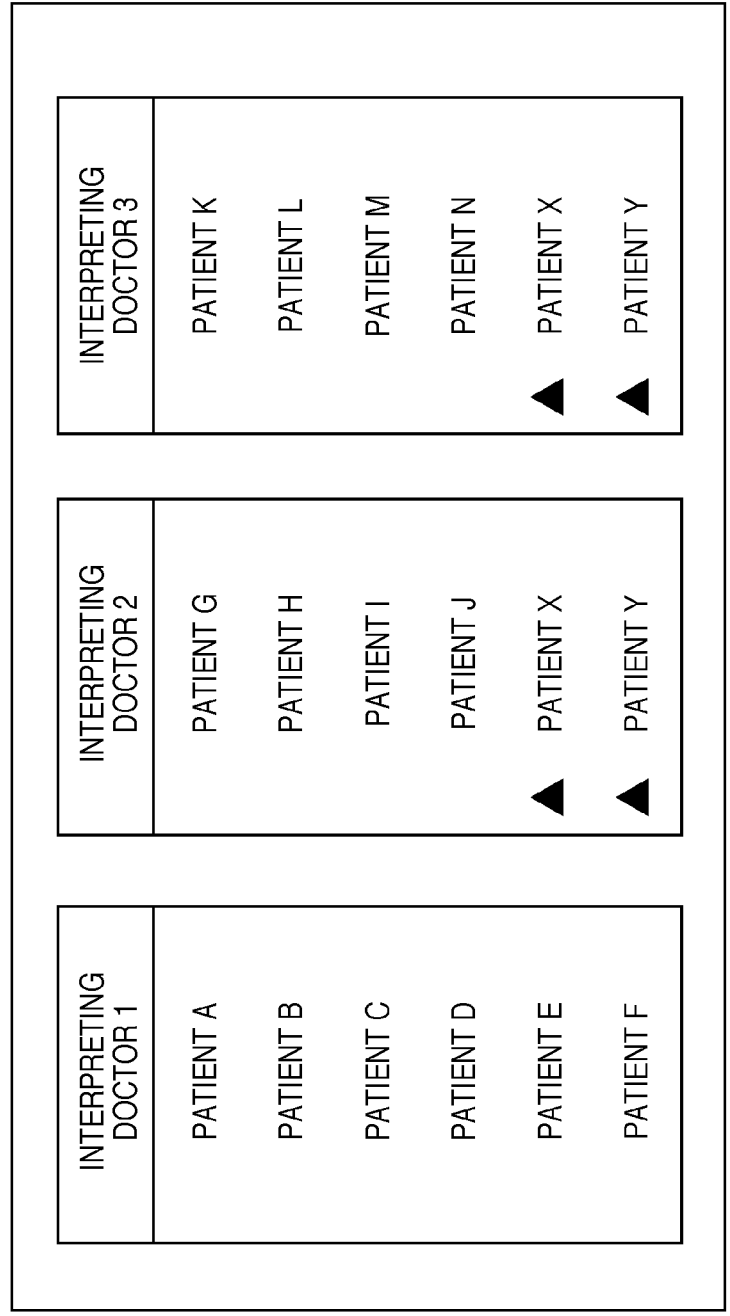
FIG. 9 is a view showing an example of the patient lists displayed on a display device 204 by an output unit 306.

FIG. 9 is a view showing an example of the patient lists displayed on the display device 204 by the output unit 306. In the case shown in FIG. 9, marks are displayed on the patient list so as to differentiate patient IDs corresponding to medical images assigned to many interpreting doctors from other patient IDs. Note that the shape and color of each mark are not limited to these, and each mark can have any shape and color as long as it is possible to recognize some difference from other patient IDs.

Consider patient list display methods. As shown in FIG. 9, patient IDs corresponding to medical images can be arranged and displayed in the interpretation sequence for each interpreting doctor. Alternatively, as shown in FIG. 10, interpreting doctor IDs can be arranged and displayed abreast of patient IDs corresponding to medical images. Displaying interpreting doctor IDs in this manner makes it possible to check a list of interpreting doctors who will take or have taken charge of the respective patients.

When interpreting doctors scheduled to take charge of the respective patients are to be displayed side by side, they can be arranged in the order of interpreting doctors decided by the selection unit 304 or can be arranged based on interpreting doctor information such as posts or experiences.

Medical images are output to a CRT, liquid crystal display, plasma display, or the like. Patient lists may be displayed on the display device 204 such as a CRT, liquid crystal display, or plasma display, or may be printed out on a paper medium by using a printer (not shown). Note that the output unit 306 shown in FIG. 2 may include a plurality of output units.

As is obvious from the above description, the medical image processing apparatus according to this embodiment is configured to decide assigned doctors at the time of interpretation of medical images, based on the medical image analysis result obtained by the image analysis unit 301 and the interpreting doctor information managed by the management unit 303.

This makes it possible to improve the overall operating efficiency when a plurality of interpreting doctors share the interpreting operation and also improve interpretation accuracy.

Second Embodiment

In the first embodiment described above, a medical image determined by the image analysis unit 301 as one that is difficult to identify (for which a flag is set) is assigned to a skilled interpreting doctor or an interpreting doctor specializing in a region in which a lesion has been detected.

However, the present invention is not limited to this, and can be configured to, for example, assign a medical image which is difficult to identify to a resident or an unexperienced doctor for education purpose. Alternatively, the present invention can be configured to automatically assign a medical image interpreted by a resident to an advising doctor who is in a position to advise residents and the like.

The first embodiment described above is also configured to assign a medical image from which no lesion has been detected by the image analysis unit 301 to a general interpreting doctor for which a corresponding modality is set.

However, the present invention is not limited to this. For example, the present invention can be configured to inhibit a resident or unexperienced interpreting doctor from setting a doctor's speciality in region or modality and to make him/her interpret all medical images from which no lesion has been detected.

In the first embodiment described above, all pieces of information registered as interpreting doctor information are handled on the same level. However, the present invention is not limited to this. For example, the present invention can be configured to set priority levels so as to handle information registered as interpreting doctor information upon weighting it.

More specifically, for example, in the case of modalities, a CT image and an MRI image are respectively set to "1" and "2". In the case of doctor's speciality in regions, a chest region, abdominal region, and head region are respectively set to "1", "2", and "3". If priority levels are set, weights are set in accordance with the priority levels.

The above setting of priority levels is an example. Besides this example, it is possible to set priority levels based on categories such as a chest region and an abdominal region.

Alternatively, it is possible to set priority levels in detail as follows. In the case of a chest region, the lung is set to "1", and the heart is set to "2".

As described above, the medical image processing apparatus according to this embodiment is basically configured to optimally assign medical images based on analysis results and interpreting doctor information and is configured to arbitrarily set a setting criterion based on a diagnosis criterion for each hospital or center.

The first embodiment described above generates patient lists in interpreting doctor decision processing and performs interpretation based on the lists. However, the present invention is not limited to this, and can be configured to dynamically change the interpretation sequence in a patient list during interpretation.

When, for example, a resident and an advising doctor are to perform double reading, the advising doctor preferably performs interpretation after the resident performs interpretation. For this purpose, this apparatus may be configured to automatically add, to a patient list for the advising doctor, a patient ID corresponding to a medical image interpreted by the resident, when the resident completes interpretation.

Figure 11A:
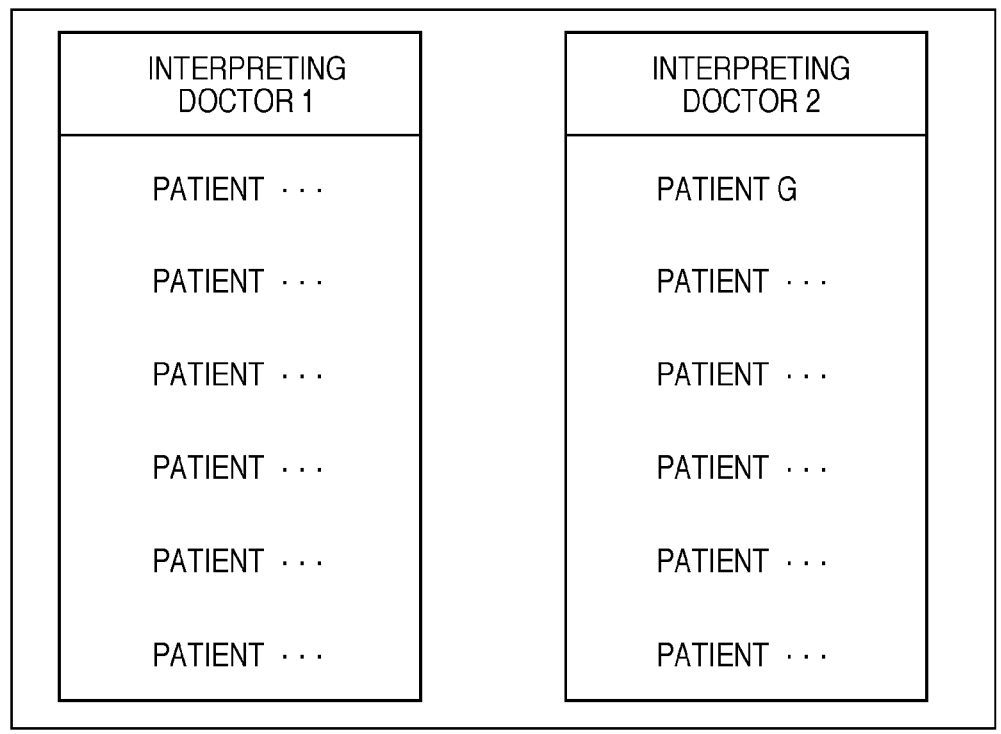
FIG. 11A is a view showing an example of patient lists.
Figure 11B:
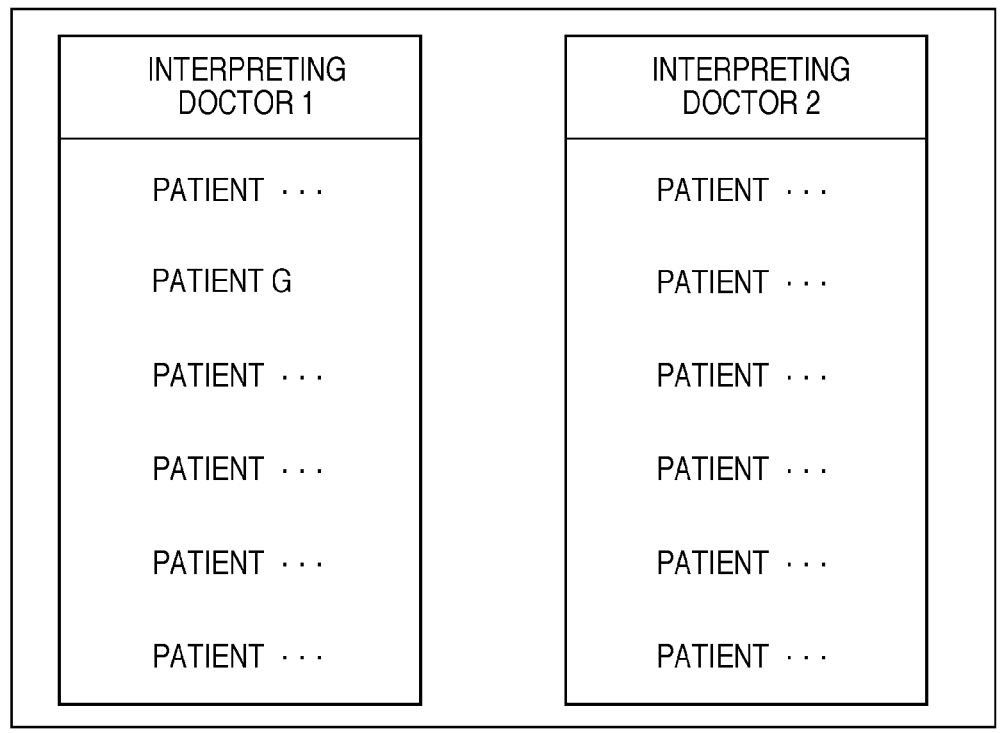
FIG. 11B is a view showing an example of patient lists.

FIGS. 11A and 11B each show an example of such patient lists. FIG. 11A shows patient lists before interpreting doctor 2 who is a resident interprets a medical image of a patient G. FIG. 11B shows a case in which the patient G is added to the patient list for interpreting doctor 1 who is an advising doctor after interpreting doctor 2 finishes interpreting a medical image of the patient G.

Assume another case in which a specific interpreting doctor stops interpretation halfway or the progress of interpretation is stagnant. In this case, it is necessary to reassign another interpreting doctor the medical image assigned to the specific interpreting doctor. For this reason, in such a case, this apparatus may be configured to add a patient ID corresponding to the medical image to a patient list for a skilled or specialized interpreting doctor. Note that in this case, the apparatus may be configured to perform no additional processing when the medical image is assigned to an interpreting doctor other than the specific interpreting doctor.

Third Embodiment

The first and second embodiments are configured to assign medical images to optimal interpreting doctors from the viewpoint of interpretation accuracy based on the analysis result obtained by the image analysis unit and interpreting doctor information.

However, the present invention is not limited to this, and can be configured to assign medical images to interpreting doctors from the viewpoint of the optimization of interpretation timings based on the additional information of each medical image and the schedule information of interpreting doctors. The details of this embodiment will be described below.

Note that the hardware arrangement of a medical image processing apparatus according to this embodiment is the same as that of the first embodiment, and hence a repetitive description will be omitted. Of the functions implemented by executing a medical image processing program, the functions of the respective units other than the management unit and the selection unit are the same as those in the first embodiment, and hence a repetitive description will be omitted. Processing in the management unit and the selection unit will be described with a focus on the differences from the first embodiment described above.

1. Management Unit

The management unit will be described first. FIG. 12 is a view showing an example of the interpreting doctor information managed by a management unit 303. The management unit 303 also manages the time schedule of interpreting doctors (information associated with the times at which medical images can be interpreted) as interpreting doctor information. In the time schedule, the dates and times at which interpreting doctors will perform interpretation are set. Note that it is possible to automatically update the time schedule on a daily basis or to collectively update it with information corresponding to several days.

2. Selection Unit

Figure 13:
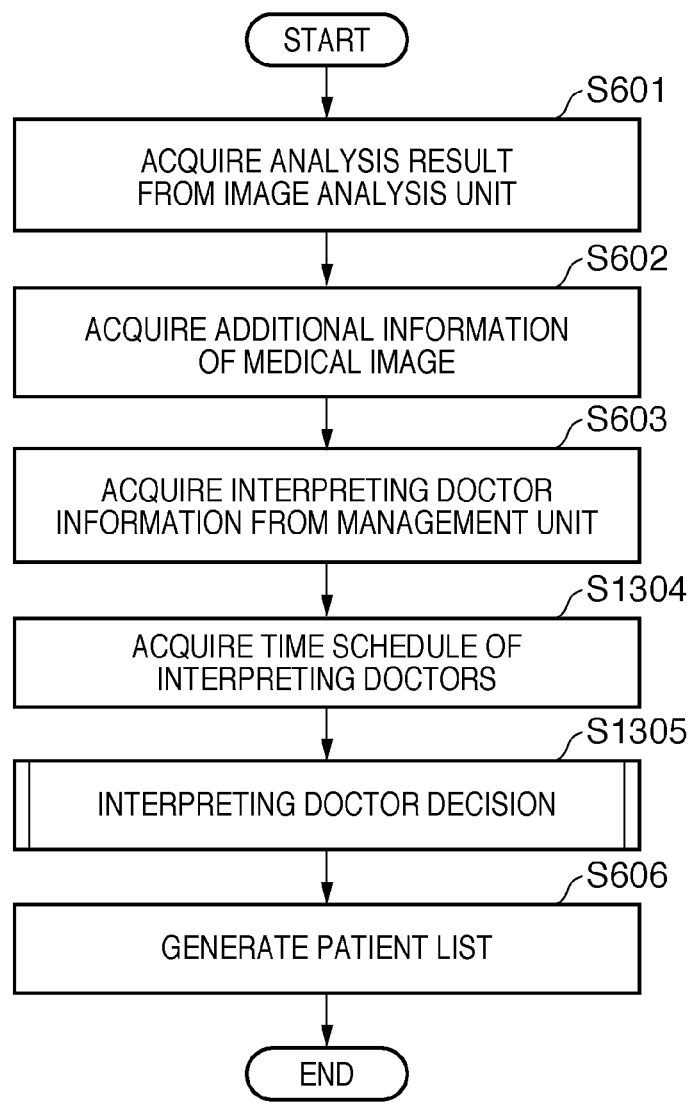
FIG. 13 is a flowchart showing a processing sequence in a selection unit 304.

Processing in a selection unit 304 will be described next with reference to the flowchart of FIG. 13. The processing in steps S601 to S603 is the same as that in the first embodiment (FIG. 6).

In step S1304, the selection unit 304 acquires the time schedule of interpreting doctors registered in the management unit 303.

In step S1305, the selection unit 304 decides interpreting doctors who will interpret medical images as assignment targets from an acquired analysis result and the time schedule of the interpreting doctors.

In step S606, a patient list for displaying a list of patients corresponding to the assigned medical images is generated for each interpreting doctor based on the interpreting doctor decision processing result in step S1305.

2.1 Details of Interpreting Doctor Decision Processing (Step S1305)

FIG. 14 is a flowchart showing the detailed processing sequence of interpreting doctor decision processing. In step S1401, it is determined whether a degree of urgency is set in the additional information of a medical image. If it is determined in step S1401 that a degree of urgency is set, the process advances to step S1402 to decide an interpreting doctor, of interpreting doctors who are currently performing interpretation, to which the medical image is to be assigned.

If it is determined in step S1401 that no degree of urgency is set, the process advances to step S1403 to determine whether an interpretation deadline is set in the additional information of the medical image.

If it is determined in step S1403 that an interpretation deadline is set, the process advances to step S1404 to decide an interpreting doctor, of interpreting doctors who perform interpretation before the interpretation deadline, to which the medical image is to be assigned.

If neither a degree of urgency nor an interpretation deadline is set, the process advances to step S1405 to decide one of the interpreting doctors scheduled to perform interpretation within a set time. Assume that in this case, a set time can be set for each hospital or interpretation center, and can be set such that interpretation should be performed within, for example, 6, 12, or 24 hr.

As is obvious from the above description, this embodiment assigns a plurality of medical images to optimal interpreting doctors based on the additional information added to the medical images obtained by a medical imaging apparatus and the time schedule of the interpreting doctors. This makes it possible to perform interpretation at optimal interpretation timings when a plurality of interpreting doctors interpret a plurality of medical images.

Fourth Embodiment

Each embodiment described above has exemplified the processing for optimizing the assignment of a plurality of medical images to a plurality of interpreting doctors. However, the present invention is not limited to this, and can be configured to optimize the interpretation sequence of medical images optimally assigned to the respective interpreting doctors.

FIG. 15 is a functional block diagram showing the functions implemented by a medical image processing program according to this embodiment. The difference from FIG. 3 is that an image sequence setting unit 1506 is newly added. Processing in the image sequence setting unit will be described below.

The image sequence setting unit 1506 sets an interpretation sequence in a patient list based on the conditions set by an interpreting doctor. For example, the interpreting doctor can designate an interpretation sequence in the order of identification difficulty, malignancy grade, interpretation deadline, or imaging time, or on a modality, imaging region, or lesion detection region basis, or at random.

Figure 16A:
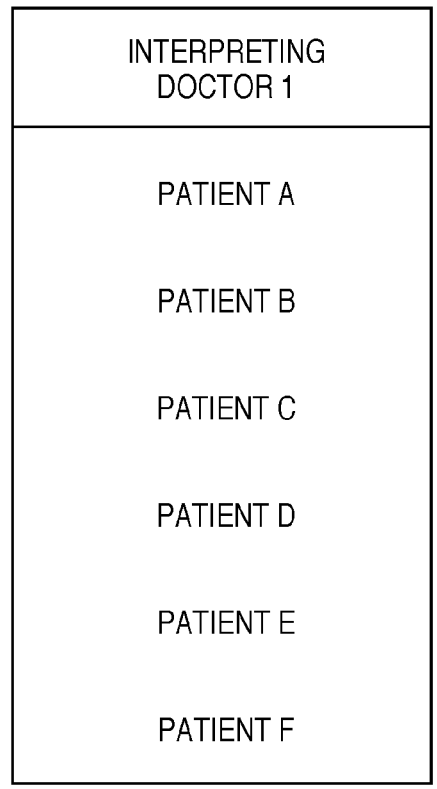
FIG. 16A is a view showing an example of a patient list.
Figure 16B:
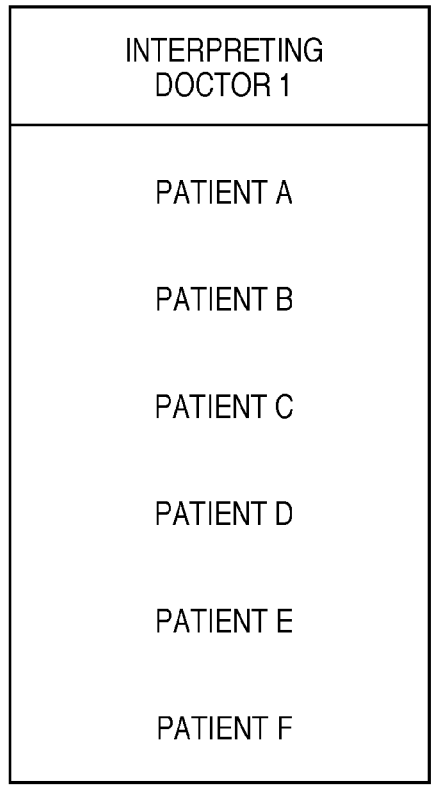
FIG. 16B is a view showing an example of a patient list.

FIGS. 16A and 16B each show an example of a patient list which is rearranged upon setting by an interpreting doctor. FIG. 16A shows an example of the patient list automatically set by a medical image processing apparatus 101. FIG. 16B shows an example of the patient list after the interpretation sequence is rearranged upon setting by the interpreting doctor.

When an interpretation sequence is to be designated in the order of identification difficulties, the patient list is rearranged in ascending order of the distances between the patterns and the Bayesian boundary between classes based on the identification result obtained by an image analysis unit 301.

When an interpretation sequence is to be designated in the order of malignancy grades, the patient list is rearranged in descending order of likelihood ratio, with a class $\omega_1$ being a malignant class when the image analysis unit 301 identifies malignancy grades.

Assume that an interpretation sequence is to be designated in the order of interpretation deadlines. In this case, when an interpretation deadline is set in the additional information of each medical image, the patient list is rearranged in ascending order of remaining time to the interpretation deadline. When an interpretation sequence is to be designated in the order of imaging times, the patient list is rearranged in the order of the times at which the medical images were obtained by the respective modalities. When an interpretation sequence is to be designated on a modality basis, the sequence is rearranged on an imaging modality basis, including an X-ray apparatus, CT apparatus, and MRI apparatus.

When an interpretation sequence is to be designated on an imaging region basis, the sequence is rearranged on an imaging region basis, including a chest region, breast region, and abdominal region. When an interpretation sequence is to be designated on a lesion detection region basis, the sequence is rearranged for the respective regions in which lesions were detected by the image analysis unit 301. That is, when the imaging range of medical images is a chest region, a medical image on which a lesion in the lung is detected and a medical image on which a lesion in the cardiovascular system is detected are rearranged in different manners. Assume that the above rearrangements each allow setting an ascending order or a descending order.

Assume that even in this case, a patient ID corresponding to a medical image set for only a specific interpreting doctor by the medical image processing apparatus is placed at a higher position in the patient list. For example, in the case of interpreting doctor 3 in FIG. 12, since the time schedule is set to 13:00 to 15:00, interpretation can be performed only within the set time. Assume therefore that the selection unit 304 preferentially places a medical image set for only a specific interpreting doctor at a higher position in the patient list so as to allow the doctor to interpret the image within the set time.

As is obvious from the above description, this embodiment allows each interpreting doctor to rearrange the medical images optically assigned to each interpreting doctor to an optimal sequence. This makes it possible to improve the interpretation accuracy and reduce oversight.

Other Embodiments

The present invention may be applied to a system constituted by a plurality of devices (e.g., a host computer, interface device, reader, and printer) or an apparatus comprising a single device (e.g., a copying machine or facsimile apparatus).

Obviously, the object of the present invention is implemented even by supplying a computer-readable storage medium storing software program codes for implementing the functions of the above embodiments to the system or apparatus. In this case, the above functions are implemented by causing the computer (or the CPU or MPU) of the system or apparatus to read out and execute the program codes stored in the storage medium. In this case, the storage medium storing the program codes constitutes the present invention.

As a storage medium for supplying the program codes, for example, a Floppy® disk, hard disk, optical disk, magnetooptical disk, CD-ROM, CD-R, magnetic tape, nonvolatile memory card, or ROM can be used.

As is obvious, the functions of the above embodiments are implemented not only when the readout program codes are executed by the computer but also when the OS (Operating System) running on the computer performs part or all of actual processing on the basis of the instructions of the program codes.

In addition, the present invention also incorporates a case in which the functions of the above embodiments are implemented after the program codes read out from the storage medium are written in the memory of a function expansion board inserted into the computer or a function expansion unit connected to the computer. That is, the present invention also incorporates a case in which the functions of the above embodiments are implemented when the program codes are written in the memory, and the CPU of the function expansion board or function expansion unit performs part or all of actual processing on the basis of the instructions of the program codes.

The present invention is not limited to the above embodiments and various changes and modifications can be made within the spirit and scope of the present invention. Therefore, to apprise the public of the scope of the present invention, the following claims are made.

The invention claimed is:

1. A medical image processing apparatus comprising:
a processor; and
a memory storing instructions that, when executed by the processor, cause the medical image processing apparatus to function as:
a selection unit configured to:
obtain lesion information relating to a medical image of an object of a plurality of medical images obtained by imaging an object using a medical imaging apparatus;
acquire additional information related to the medical image;
acquire time schedules of one or more doctors of a plurality of doctors;
determine whether a degree of urgency is set as a part of the additional information related to the medical image;
in a case where a determination is made that the degree of urgency is set, assign the medical image to a doctor of the plurality of doctors who is currently performing interpretation;
in a case where a determination is made that the degree of urgency has not been set, determine whether an interpretation deadline has been set as a part of the additional information related to the medical image;
in a case where a determination is made that the interpretation deadline has been set, assign the medical image to a doctor of the plurality of doctors whose acquired time schedule is set within the interpretation deadline; and
in a case where a determination is made that the interpretation deadline has not been set, assign the medical image to a doctor of the plurality of doctors whose acquired time schedule is set within a set time; and
an output unit configured to output, to a display unit, information corresponding to the doctor to which the medical image is assigned, together with the information corresponding to the assigned medical image.

2. The medical image processing apparatus according to claim 1,
wherein the instructions, when executed by the processor, further cause the medical image processing apparatus to analyze the medical image of an object of a plurality of medical images, to detect the lesion in the medical image.

3. The medical image processing apparatus according to claim 1, wherein the result of the analysis includes information indicating the presence or absence of a lesion and information indicating identification difficulty of the lesion.

4. The medical image processing apparatus according to claim 1, wherein the result of the analysis includes information indicating the presence or absence of a lesion and information indicating the medical importance of the lesion.

5. The medical image processing apparatus according to claim 1, further comprising a storage unit configured to store information indicating attributes of each of the plurality of doctors with respect to the interpretation of a specific lesion and identification information of the each of the plurality of doctors, which are associated with each other,
wherein the instructions, when executed by the processor, further cause the medical image processing apparatus to decide a doctor to interpret the medical image by using the result of the analysis and the information stored in the storage unit.

6. A medical image processing method comprising:
obtaining, by a processor, lesion information relating to a medical image of a plurality of medical images obtained by imaging an object using a medical imaging apparatus;
acquiring additional information related to the medical image;
acquiring time schedules of one or more doctors of a plurality of doctors;

determining whether a degree of urgency is set as a part of the additional information related to the medical image;

in a case where a determination is made that the degree of urgency is set, assigning the medical image to a doctor of the plurality of doctors who is currently performing interpretation;

in a case where a determination is made that the degree of urgency has not been set, determining whether an interpretation deadline has been set as a part of the additional information related to the medical image;

in a case where a determination is made that an interpretation deadline has been set, assigning the medical image to a doctor of the plurality of doctors whose acquired time schedule is set within the interpretation deadline;

in a case where a determination is made that the interpretation deadline has not been set, assigning the medical image to a doctor of the plurality of doctors whose acquired time schedule is set within a set time; and outputting, to a display unit, information corresponding to the doctor to which the medical image is assigned, together with information corresponding to the assigned medical image.

7. A non-transitory computer-readable storage medium storing a program which causes a computer to execute a medical image processing method, the method comprising:

obtaining, by a processor, lesion information relating to a medical image of a plurality of medical images obtained by imaging an object using a medical imaging apparatus;

acquiring additional information related to the medical image;

acquiring time schedules of one or more doctors of a plurality of doctors;

determining whether a degree of urgency is set as a part of the additional information related to the medical image;

in a case where a determination is made that the degree of urgency is set, assigning the medical image to a doctor of the plurality of doctors who is currently performing interpretation;

in a case where a determination is made that the degree of urgency has not been set, determining whether an interpretation deadline has been set as a part of the additional information related to the medical image;

in a case where a determination is made that the interpretation deadline has been set, assigning the medical image to a doctor of the plurality of doctors whose acquired time schedule is set within the interpretation deadline;

in a case where a determination is made that the interpretation deadline has not been set, assigning the medical image to a doctor of the plurality of doctors whose acquired time schedule is set within a set time; and outputting, to a display unit, information corresponding to the doctor to which the medical image is assigned, together with information corresponding to the assigned medical image.

8. A medical image processing apparatus which decides assigned doctors so as to allow a plurality of doctors to share in interpreting a plurality of medical images obtained by imaging an object using a medical imaging apparatus, comprising:

a processor; and a memory storing instructions that, when executed by the processor, cause the medical image processing apparatus to:

analyze a medical image, of the plurality of medical images, which serves as an assignment;

output an analysis result;

acquire information associated with a medical imaging apparatus used to obtain the medical image as an assignment target;

acquire additional information related to the medical image;

register information representing a specialty of each doctor with respect to interpretation of a specific lesion and information representing a specialty of each doctor with respect to interpretation of a medical image obtained by imaging by a specific medical imaging apparatus;

acquire time schedules of one or more doctors of the plurality of doctors;

determine whether a degree of urgency is set as a part of the additional information related to the medical image;

in a case where a determination is made that the degree of urgency is set, assign a doctor of the plurality of doctors to the medical image as the assignment target based on information which is registered and represents a specialty of each doctor with respect to interpretation of a specific lesion, the doctor of the plurality of doctors being who is currently performing interpretation;

in a case where a determination is made that the degree of urgency has not been set, determine whether an interpretation deadline has been set as a part of the additional information related to the medical image;

in a case where a determination is made that the interpretation deadline has been set, assign the medical image to a doctor of the plurality of doctors whose acquired time schedule is set within the interpretation deadline; and in a case where a determination is made that the interpretation deadline has not been set, assign the medical image to a doctor of the plurality of doctors whose acquired time schedule is set within a set time.

9. A medical image processing apparatus which decides assigned doctors so as to allow a plurality of doctors to share in interpreting a plurality of medical images obtained by imaging an object using a medical imaging apparatus, comprising:

a processor; and a memory storing instructions that, when executed by the processor, cause the medical image processing apparatus to:

analyze a medical image, of the plurality of medical images, which serves as an assignment;

output an analysis result;

acquire information associated with a medical imaging apparatus used to obtain the medical image as an assignment target;

acquire additional information related to the medical image;

register information representing a specialty of each doctor with respect to interpretation of a specific lesion and information representing a specialty of each doctor with respect to interpretation of a medical image obtained by imaging by a specific medical imaging apparatus;

acquire time schedules of one or more doctors of the plurality of doctors;

determine whether a degree of urgency is set as a part of the additional information related to the medical image;

in a case where a determination is made that the degree of urgency is set, assign a doctor of the plurality of doctors to the medical image as the assignment target based on information which is registered and represents a specialty of each doctor with respect to interpretation of a medical image obtained by imaging by a specific medical imaging apparatus, the doctor of the plurality of doctors being who is currently performing interpretation;

in a case where a determination is made that the degree of urgency has not been set, determine whether an interpretation deadline has been set as a part of the additional information related to the medical image;

in a case where a determination is made that the interpretation deadline has been set, assign the medical image to a doctor of the plurality of doctors whose acquired time schedule is set within the interpretation deadline; and in a case where a determination is made that the interpretation deadline has not been set, assign the medical image to a doctor of the plurality of doctors whose acquired time schedule is set within a set time.

10. A medical image processing apparatus comprising:
a processor; and
a memory storing instructions that, when executed by the processor, cause the medical image processing apparatus to function as:
a selection unit configured to:
obtain lesion information relating to a medical image of a plurality of medical images;
acquire additional information related to the medical image including a degree of urgency and an interpretation deadline;
acquire time schedules of one or more doctors of a plurality of doctors;
determine whether a degree of urgency is set as a part of the additional information of the medical image;
in a case where a determination is made that the degree of urgency is set, assign the medical image to a doctor of the plurality of doctors, the doctor being assigned for interpreting the medical image and being who is currently performing interpretation;
in a case where a determination is made that the degree of urgency has not been set, determine whether an interpretation deadline has been set as a part of the additional information of the medical image;
in a case where a determination is made that the interpretation deadline has been set, assign the medical image to a doctor of the plurality of doctors whose acquired time schedule is set within the interpretation deadline; and
in a case where a determination is made that the interpretation deadline has not been set, assign the medical image to a doctor of the plurality of doctors whose acquired time schedule is set within a set time; and
an output unit configured to output, to an external apparatus, information corresponding to the doctor to which the medical image is assigned, together with information corresponding to the assigned medical image.

11. The medical image processing apparatus according to claim 10, wherein the instructions, when executed by the processor, further cause the medical image processing apparatus to analyze a medical image of a plurality of medical images, to detect a lesion in the medical image.

12. The medical image processing apparatus according to claim 11, wherein the result of the analysis includes information indicating the presence or absence of a lesion and information indicating identification difficulty of the lesion.

13. The medical image processing apparatus according to claim 11, wherein the result of the analysis includes information indicating the presence or absence of a lesion and information indicating the medical importance of the lesion.

14. The medical image processing apparatus according to claim 11, further comprising a storage unit configured to store information indicating attributes of each of the plurality of doctors with respect to the interpretation of a specific lesion and identification information of the each of the plurality of doctors, which are associated with each other,
wherein the instructions, when executed by the processor, further cause the medical image processing apparatus to decide a doctor to interpret the medical image by using the result of the analysis and the information stored in the storage unit.

15. A medical image processing method comprising:
obtaining, by a processor, lesion information relating to a medical image of a plurality of medical images obtained by imaging an object using a medical imaging apparatus;
acquiring additional information related to the medical image;
acquiring time schedules of one or more doctors of a plurality of doctors;
determining whether a degree of urgency is set as a part of the additional information of the medical image;
in a case where a determination is made that the degree of urgency is set, assigning the medical image to a doctor of the plurality of doctors, the doctor being assigned for interpreting the medical image and being who is currently performing interpretation;
in a case where a determination is made that the degree of urgency has not been set, determining whether an interpretation deadline has been set as a part of the additional information of the medical image;
in a case where a determination is made that the interpretation deadline has been set, assigning the medical image to a doctor of the plurality of doctors whose acquired time schedule is set within the interpretation deadline;
in a case where a determination is made that the interpretation deadline has not been set, assigning the medical image to a doctor of the plurality of doctors whose acquired time schedule is set within a set time; and
outputting, to an external apparatus, information corresponding to the doctor to which the medical image is assigned, together with information corresponding to the assigned medical image.

16. A medical image processing system comprising:
an imaging device configured to capture a plurality of medical images; and a medical image processing apparatus comprising:
- a processor; and
- a memory storing instructions that, when executed by the processor, cause the medical image processing apparatus to function as:
  - a selection unit configured to:
    - obtain lesion information relating to a medical image of an object of the plurality of medical images;
    - acquire additional information related to the medical image;
    - acquire time schedules of one or more doctors of a plurality of doctors;
    - determine whether a degree of urgency is set as a part of the additional information related to the medical image;
    - in a case where a determination is made that the degree of urgency is set, assign the medical image to a doctor of the plurality of doctors who is currently performing interpretation;
    - in a case where a determination is made that the degree of urgency has not been set, determine whether an interpretation deadline has been set as a part of the additional information related to the medical image;
    - in a case where a determination is made that the interpretation deadline has been set, assign the medical image to a doctor of the plurality of doctors whose acquired time schedule is set within the interpretation deadline; and
    - in a case where a determination is made that the interpretation deadline has not been set, assign the medical image to a doctor of the plurality of doctors whose acquired time schedule is set within a set time; and
  - an output unit configured to output, to a display unit, information corresponding to the doctor to which the medical image is assigned, together with the information corresponding to the assigned medical image.

* * * * *